US009072468B2

(12) United States Patent
Buchman et al.

(10) Patent No.: US 9,072,468 B2
(45) Date of Patent: Jul. 7, 2015

(54) APPARATUS AND METHODS FOR ACOUSTICALLY OR MECHANICALLY STIMULATING A COCHLEA AND INTRACOCHLEAR RECORDING OF MECHANICALLY OR ACOUSTICALLY EVOKED AUDITORY POTENTIALS IN THE COCHLEA

(71) Applicant: The University of North Carolina at Chapel Hill, Chapel Hill, NC (US)

(72) Inventors: Craig A. Buchman, Chapel Hill, NC (US); Oliver F. Adunka, Durham, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 13/949,975

(22) Filed: Jul. 24, 2013

(65) Prior Publication Data
US 2014/0094712 A1 Apr. 3, 2014

Related U.S. Application Data

(63) Continuation of application No. 12/422,926, filed on Apr. 13, 2009, now abandoned, which is a continuation-in-part of application No. PCT/US2007/017614, filed on Aug. 8, 2007.

(60) Provisional application No. 60/851,400, filed on Oct. 13, 2006.

(51) Int. Cl.
*A61B 5/00* (2006.01)
*A61B 5/12* (2006.01)
(Continued)

(52) U.S. Cl.
CPC ............. *A61B 5/121* (2013.01); *A61B 5/04845* (2013.01); *A61N 1/0541* (2013.01)

(58) Field of Classification Search
CPC .... A61B 5/121; A61B 5/128; A61B 5/04845; A61N 1/0541; A61N 1/36032; A61N 1/37223; A61N 1/3787
USPC ............... 600/554, 559; 607/55–57, 136, 137
See application file for complete search history.

(56) References Cited

U.S. PATENT DOCUMENTS

| 4,400,590 A | 8/1983 | Michelson |
| 4,532,930 A | 8/1985 | Crosby et al. |

(Continued)

FOREIGN PATENT DOCUMENTS

| WO | WO 98/36711 | 8/1998 |
| WO | WO 02/082982 A1 | 10/2002 |

OTHER PUBLICATIONS

Final Office Action for U.S. Appl. No. 12/422,926 (Jan. 24, 2013).
(Continued)

*Primary Examiner* — Max Hindenburg
(74) *Attorney, Agent, or Firm* — Jenkins, Wilson, Taylor & Hunt, P.A.

(57) ABSTRACT

An apparatus for acoustic or mechanical stimulation of a cochlea and measurement of acoustically or mechanically evoked electrophysiologic responses from the cochlea is provided. In one example, the apparatus includes an acoustic stimulator for generating an acoustic signal and an electrophysiologic response measuring device positioned proximal the cochlea or within the cochlea for measuring an acoustically evoked electrophysiologic response to the acoustic signal. Methods of utilizing the apparatus for diagnostic and therapeutic procedures related to hearing impairment are also provided.

27 Claims, 7 Drawing Sheets

(51) Int. Cl.
*A61B 5/0484* (2006.01)
*A61N 1/05* (2006.01)

(56) References Cited

U.S. PATENT DOCUMENTS

| | | | |
|---|---|---|---|
| 4,592,359 A | | 6/1986 | Galbraith |
| 4,947,844 A | | 8/1990 | McDermott |
| 5,012,814 A | | 5/1991 | Mills et al. |
| 5,776,172 A | | 7/1998 | Schulman et al. |
| 5,776,179 A | | 7/1998 | Ren et al. |
| 5,833,626 A | * | 11/1998 | Leysieffer ............... 600/559 |
| 5,999,856 A | | 12/1999 | Kennedy |
| 6,067,474 A | | 5/2000 | Schulman et al. |
| 6,231,604 B1 | | 5/2001 | Von Ilberg |
| 6,640,121 B1 | | 10/2003 | Telischi et al. |
| 6,916,291 B2 | | 7/2005 | Givens et al. |
| 6,980,864 B2 | | 12/2005 | Faltys et al. |
| 2002/0004516 A1 | | 1/2002 | Stutzmann et al. |
| 2005/0131272 A1 | | 6/2005 | Waldmann |
| 2005/0261748 A1 | * | 11/2005 | van Dijk ............... 607/57 |
| 2007/0015727 A1 | * | 1/2007 | Puel et al. ............... 514/49 |
| 2009/0259140 A1 | | 10/2009 | Buchman et al. |

OTHER PUBLICATIONS

Applicant-Initiated Interview Summary for U.S. Appl. No. 12/422,926 (Oct. 29, 2012).
Non-Final Official Action for U.S. Appl. No. 12/422,926 (Oct. 10, 2012).
Extended European Search Report for European Application No. 07836613.5 (Sep. 21, 2012).
Patent Examination Report No. 1 for Australian Patent Application No. 2007313412 (Jun. 22, 2012).
Final Official Action for U.S. Appl. No. 12/422,926 (Apr. 16, 2012).
Applicant-Initiated Interview Summary for U.S. Appl. No. 12/422,926 (Feb. 7, 2012).
Non-Final Official Action for U.S. Appl. No. 12/422,926 (Sep. 6, 2011).
Communication of European publicaiton number and information on the application of Article 67(3) EPC for European Application No. 07836613.5 (Jun. 10, 2009).
Notifcation of Transmittal of the International Search Report and the Written Opinion of the International Searching Authority, or the Declaration for International Application No. PCT/US07/17614 (Jan. 29, 2008).
Adunka et al., "Monitoring of Cochlear Function During Cochlear Implantation," Laryngoscope, vol. 116, No. 6, pp. 1017-1020 (Jun. 2006).
Chen et al., "A Method for Intracochlear Drug Delivery in the Mouse," Journal of Neuroscience Methods, vol. 150, No. 1, pp. 67-73 (2006).
Fraysse et al., "Residual Hearing Conservation and Electroacoustic Stimulation with the Nucleus 24 Contour Advance Cochlear Implant," Otology & Neurotology, vol. 27, pp. 624-633 (2006).
Tang et al., "Sensorineural Hearing Loss: Potential Therapies and Gene Targets for Drug Development," IUBMB Life, vol. 58, No. 9, pp. 525-530 (Sep. 2006).
Gantz et al., "Preservation of Hearing in Cochlear Implant Surgery: Advantages of Combined Electrical and Acoustical Speech Processing," Laryngoscope, vol. 115, pp. 796-802 (May 2005).
Garnham et al., "Protecting Hearing—Optimising Pharmacological Intervention," MED EL. (Oct. 2005).
James et al., "Preservation of Residual Hearing with Cochlear Implantation: How and Why," Acta Oto-Laryngologica, vol. 125, pp. 481-491 (2005).
Kiefer et al., "Combined Electric and Acoustic Stimulation of the Auditory System: Results of a Clinical Study," Audiology & Neurotology, vol. 10, pp. 134-144 (2005).
Adunka et al., "Development and Evaluation of an Improved Cochlear Implant Electrode Design for Electric Acoustic Stimulation," Laryngoscope, vol. 114, pp. 1237-1241 (Jul. 2004).
Adunka et al., "Cochlear Implantation Via the Round Window Membrane Minimizes Trauma to Cochlear Structures: A Histologically Controlled Insertion Study," Acta Otolaryngol, vol. 124, pp. 807-812 (2004).
Battmer et al., "Evaluation of the Neural Response Telemetry (NRT) Capabilities of the Nucleus Research Platform 8: Initial Results from the NRT Trial," International Journal of Audiology, vol. 43, pp. S10-S15 (2004).
Gantz et al., "Combining Acoustic and Electrical Speech Processing: Iowa/Nucleus Hybrid Implant," Acta Otolaryngol, vol. 124, pp. 344-347 (2004).
Gstoettner et al., "Hearing Preservation in Cochlear Implantation for Electric Acoustic Stimulation," Acta Otolaryngol, vol. 124, pp. 348-352 (2004).
Kiefer et al., "Conservation of Low-Frequency Hearing in Cochlear Implantation," Acta Otolaryngol, vol. 124, pp. 272-280 (2004).
Light et al., "Transtympanic Perfusion: Indications and Limitations," Current Opinion in Otolaryngology & Head and Neck Surgery, vol. 12, pp. 378-383 (2004).
Mason, "Electrophysiologic and Objective Monitoring of the Cochlear Implant During Surgery: Implementation, Audit and Outcomes," International Journal of Audiology, vol. 43, pp. S33-S38 (2004).
Gantz et al., "Combining Acoustic and Electrical Hearing," Laryngoscope, vol. 113, pp. 1726-1730 (Oct. 2003).
Schwaber, "Transtympanic Gentamicin Perfusion for the Treatment of Meniere's Disease," Otolaryngologic Clinics of North America, vol. 35, pp. 287-295 (2002).
Prieskorn et al., "Technical Report: Chronic and Acute Intracochlear Infusion in Rodents," Hearing Research, vol. 140, pp. 212-215 (2000).
Shallop et al., "Neural Response Telemetry with the Nucleus C124M Cochlear Implant," Laryngoscope, vol. 109, No. 11, pp. 1755-1759 (Nov. 1999).
von Ilberg et al., "Electric-Acoustic Stimulation of the Auditory System," ORL, vol. 61, pp. 334-340 (1999).
McElveen et al., "Modifying the Translabyrinthine Approach to Preserve Hearing During Acoustic Tumour Surgery," The Journal of Laryngology and Otology, vol. 105, pp. 34-37 (Jan. 1991).
Kemp, "Otoacoustic Emissions, Travelling Waves and Cochlear Mechanisms," Hearing Research, vol. 22, pp. 95-104 (1986).

\* cited by examiner

APPARATUS AND METHODS FOR ACOUSTICALLY OR MECHANICALLY STIMULATING A COCHLEA AND INTRACOCHLEAR RECORDING OF MECHANICALLY OR ACOUSTICALLY EVOKED AUDITORY POTENTIALS IN THE COCHLEA

PRIORITY CLAIM

This application is a continuation of U.S. patent application Ser. No. 12/422,926, filed Apr. 13, 2009, which is a continuation-in-part of PCT International Patent Application No. PCT/US2007/017614, filed Aug. 8, 2007, which claims the benefit of U.S. Provisional Patent Application Ser. No. 60/851,400 filed Oct. 13, 2006, the disclosures of which are incorporated herein by reference in their entireties.

TECHNICAL FIELD

The presently disclosed subject matter relates to an apparatus for mechanical or acoustic stimulation of the cochlea and measurement of an electrophysiologic response to the mechanical or acoustic stimulation and methods of using the apparatus. In particular, the presently disclosed subject matter relates to an apparatus having an acoustic or mechanical stimulator for generating acoustically or mechanically evoked electrophysiologic responses in the cochlea and an intracochlear measuring device for recording these responses. The presently disclosed subject matter further relates to methods of using the apparatus for evaluating hearing impairment and selecting treatment therapies based on the evaluation using the apparatus disclosed herein.

BACKGROUND

Hearing in humans requires conduction of the acoustic signal to the inner ear by way of the external auditory canal, tympanic membrane, and ossicles (i.e., malleus, incus, and stapes). Vibration of the stapes bone (i.e., the $3^{rd}$ ossicle) within the oval window of the inner ear sets the inner ear fluids in motion thereby inducing activation of hair cells in the cochlea. Hair cell activation results in cochlear nerve fiber depolarization, ultimately leading to central auditory pathway stimulation within the brainstem.

Hearing impairments can be classified as either conductive, resulting from pathologies of the external auditory canal, tympanic membrane, and/or ossicles, or sensorineural. Sensorineural hearing losses (SNHL) most commonly result from either hair cell loss within the cochlea or as a consequence cochlear nerve disorders. By far, the most common factor for SNHL is hair cell loss. Although hair cell losses can occur throughout the cochlea, the most commonly involved regions are the high frequency (high pitch) regions.

The cochlea has a tonotopical arrangement, which means that tones close to each other in terms of frequency are received by hair cells in topologically neighboring regions of the cochlea (FIG. 1). In general, hair cells in the basal region (base) of the cochlea are activated by high frequency sound, and hair cells in the apical region (apex) of the cochlea are activated by low frequency sound. As such, hair cell losses occur most commonly in the basal regions of the cochlea, resulting in high frequency hearing impairment.

Effective hearing impairment treatment necessitates accurate determination of the cause and/or extent of hearing impairment. For example, to provide an effective and specific treatment for a hearing impairment, it is desirable to determine whether hearing impairment is conductive or sensorineural, and if sensorineural, whether it is a result of hair cell loss or neural disorder. Further, if hearing impairment results from loss of hair cell function, it would be desirable to determine the topological extent of hair cell loss to better tailor a treatment specifically for the hearing deficit. Present technologies for measuring hearing impairment are unable to provide a complete and accurate determination of the cause and/or extent of hearing impairment, particularly with regard to assessment of hair cell function.

Site of lesion testing within the auditory system is indirect, as cochlear and central nervous system biopsy is both impractical and would result in hearing loss. Present methods for measurement of hair cell function include evoked-otoacoustic emissions (OAEs) (Kemp, 1986), auditory brainstem response (ABR) testing, and behavioral audiograms. For almost 20 years, otoacoustic emissions (measure of hair cell motion and resultant sound from the hair cell motion) have been relied upon to provide information about the functional status of the inner ear. Due to the specificity of OAEs for outer hair cells, this technique can be sensitive in the early diagnosis of hair cell pathology. However, beyond about 40 decibels (dB) of hearing loss, OAEs are lost, making further assessment impossible. Moreover, the recording mechanism relies on several factors outside the inner ear, making OAE testing both indirect and inaccurate during times of pathology.

Another way to potentially evaluate hair cell function is to record ABR after stimulating the cochlea acoustically through a microphone in the external auditory canal. The electrical activity of the auditory pathways is recorded and filtered from the electrical activity of the brain. The earliest electrical potentials observed with this method are termed the cochlear microphonic potential. The cochlear microphonic potential is a measure of summated inner ear hair cell function and thus can provide some information about the overall functional status of the cochlea. ABR recordings, however, are recorded via far field electrodes mounted on the scalp of the subject. Using this method, the electrical responses of the cochlear microphonics are buried in the much stronger electrical activity of the auditory nerve (compound action potential). Usually, only in special cases where the auditory nerve fires in a dys-synchronous manner do cochlear microphonics become evident in the far field recordings. Moreover, since the cochlear microphonic potential is an averaged and summated vector potential, measurements from the various anatomic regions within the cochlea to determine the extent and range of hearing impairment are not possible with this technique.

Other recording sites for auditory potentials are the external auditory canal and the surface of the promontory in the middle ear. In contrast to far-field electrodes mounted on the scalp of the subject, these recording sites provide a better signal-to-noise ratio and can furnish greater response amplitudes at the same stimulus intensity levels, facilitating the recording of much smaller responses. Since two main electrical potentials, the cochlear microphonic (stemming from hair cells) and the compound action potential (summation potential from spiral ganglion cells as the first neural response), are recorded, this technique has been termed electrocochleography (ECochG). Due to the close anatomic relationship of the basal cochlear turn and the recording sites in the external auditory canal or the promontory, the cochlear microphonic potential is believed to be mainly a result of basal cochlear hair cells with a negligible fraction of apical hair cell contribution. Thus, this technique does not allow for measurement of apical hair cell function.

Present methods for measuring hearing deficiency, and specifically for measuring hair cell functionality, are insufficient to meet the needs of specific and accurate measurement of hair cells. As such, there is an unmet need for direct and accurate measurement of acoustically or mechanically stimulated electrophysiologic activity.

SUMMARY

This Summary describes several examples of the presently disclosed subject matter, and in many cases lists variations and permutations of these examples. This Summary is merely exemplary of the numerous and varied examples. Mention of one or more representative features of a given example is likewise exemplary. Such an example can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

According to one aspect of the presently disclosed subject matter, an apparatus for acoustic and/or mechanical stimulation and electrophysiologic response measurement of a cochlea is provided. The apparatus can comprise an acoustic or mechanical stimulator and an electrophysiologic response-measuring device. An acoustic stimulator generates an acoustic signal and can be positioned within an external auditory canal of a subject. In another example, the acoustic stimulator is positioned outside the external auditory canal, such as utilizing a free-field speaker or a headphone speaker. Also mechanical energy can be used to stimulate the cochlea. Specifically, a mechanical or vibrotactile stimulator can drive the ossicular chain or the other parts of the middle ear to provide cochlear stimulation. Another possible mode of stimulation would be to directly drive the round or oval window via a mechanical stimulator. Yet another possible method for stimulating the cochlea would be to apply mechanical energy via a bone vibration device.

The measuring device may be positioned inside the cochlea and measures an electrophysiologic response by the cochlea (e.g., resulting from hair cells within the cochlea) or the auditory neurons of the spiral ganglion to the acoustic or mechanical signal.

The acoustic stimulator can comprise a generator for generating the acoustic signal and a speaker that transmits the acoustic signal. The acoustic signal can be sound waves at a predetermined frequency range of from about 20 Hertz to about 20,000 Hertz. The acoustic signal generates an electrophysiologic response that is measured by the measuring device. Likewise, a mechanical stimulator can be used to stimulate the cochlea in this same frequency range.

The electrophysiologic response can be an acoustically or mechanically evoked electrical potential generated by activation of hair cells and/or spiral ganglion cells. The response-measuring device measures the electrophysiologic events with at least one sampling window of from about 0.2 milliseconds to about 100 milliseconds. The measuring device comprises at least one electrode for measuring the electrophysiologic responses and can include an array of electrodes. The measuring device is positioned in close proximity to the hair cells within the cochlea and can in some embodiments be positioned within the scala tympani of the cochlea.

The acoustic or mechanical stimulator and the measuring device can in some embodiments be in communication by way of a trigger. The trigger synchronizes activation of the acoustic or mechanical stimulator to generate the acoustic or mechanical signal and activation of the measuring device to measure the electrophysiologic responses in a temporary synchronized manner. In one example, the trigger may be a signal generated by the measuring device to activate the mechanical or acoustic stimulator. In another example, the trigger may be a signal generated by the mechanical or acoustic stimulator to activate the measuring device.

The presently disclosed subject matter further provides method of measuring cochlear responses to an acoustic or mechanical signal. The method comprises acoustically or mechanically stimulating a cochlea with an acoustic or mechanical signal and measuring an electrophysiologic response by the cochlea to the acoustic or mechanical signal. The method comprises generating the acoustic or mechanical signal with an acoustic or mechanical stimulator disclosed herein. An electrophysiologic response-measuring device measures the electrophysiologic responses from within the cochlea and thus is believed to provide a more direct measure of cochlear function than OAE and ABR testing, for example, which rely on measuring devices located outside of the cochlea.

In another example of the presently disclosed subject matter, a method of selecting a hearing impairment treatment therapy is provided. A cochlea is acoustically or mechanically stimulated with an acoustic or mechanical signal. An electrophysiologic response by the cochlea (e.g., a hair cell or neural response) to the acoustic or mechanical signal is then measured. A hearing impairment in the cochlea is determined based on the measured electrophysiologic response. A therapy based on the determined hearing impairment is then selected. Determining the hearing impairment can include mapping tonotopic functionality of the cochlea (i.e., correlating physical locations of functioning hair cells in the cochlea to acoustically-detected frequencies and impairments thereof). In some embodiments, the therapy is selected from the group consisting of a cochlear implant, a drug, a gene therapy, a stem cell therapy, and combinations thereof. Further, in some embodiments, the therapy is a cochlear implant implemented as a component of an electric-acoustic stimulation therapy.

Accordingly, it is an object of the presently disclosed subject matter to provide methods and apparatus for intracochlear recording of acoustically or mechanically evoked auditory potentials. This object is achieved in whole or in part by the presently disclosed subject matter.

An object of the presently disclosed subject matter having been stated above, other objects and advantages will become apparent to those of ordinary skill in the art after a study of the following description of the presently disclosed subject matter and non-limiting examples.

DETAILED DESCRIPTION

Figure 1:
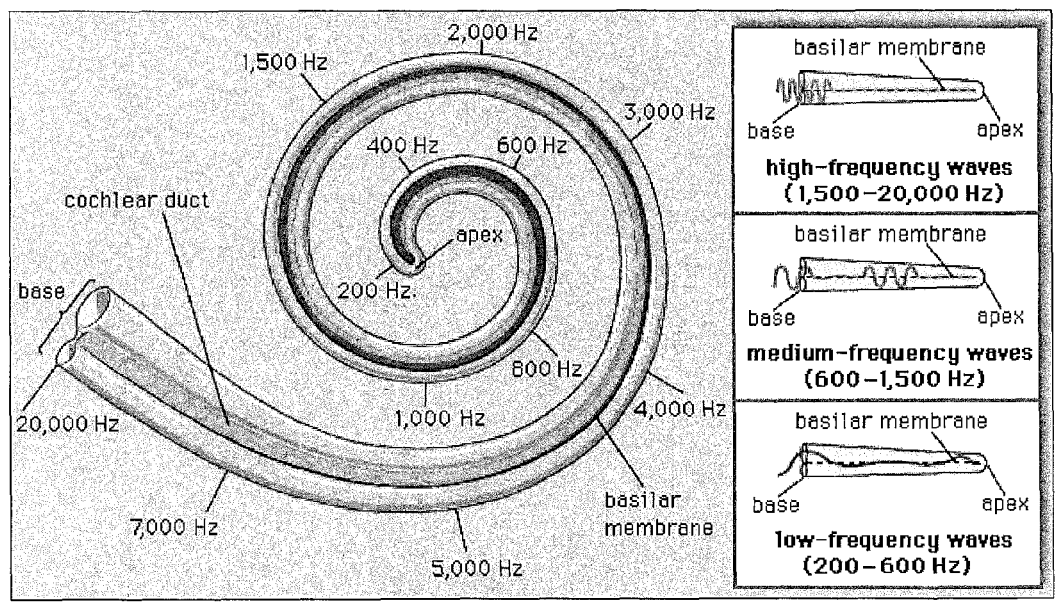
FIG. 1 is a schematic drawing showing tonotopic arrangement of the cochlea. High frequencies are located basally and low frequencies are located apically.

The presently disclosed subject matter provides apparatus for acoustic or mechanical stimulation of a cochlea and intracochlear recording of acoustically or mechanically evoked electrophysiologic responses in the cochlea for use in diagnostic and/or therapeutic procedures related to sensorineural hearing impairment. "Hearing impairment", as used herein, can refer to a measurable reduction in hearing capabilities (over a broad and/or narrow range of frequencies) as compared to a comparable normal subject not suffering from measurable hearing impairment. The presently disclosed subject matter allows for measuring hearing impairment in a subject by direct measurement of acoustically or mechanically evoked electrophysiologic responses (e.g., hair cell or neural activation, including for example auditory neurons of the spiral ganglion) in the subject, which can provide data with improved signal-to-noise ratio (i.e., greater intensity of the signal and/or lower intensity of noise) and therefore a more accurate determination of sensorineural hearing impairment with tonotopic specificity by direct measure of hair cell activity and/or neural responses from the auditory system.

By positioning a measuring device as disclosed herein within the inner ear, hair cell activity or activity within the spiral ganglion in the form of electrical potentials can be measured directly adjacent to the cells of origin, rather than indirectly as provided by present techniques. A direct hair-cell evaluation can provide a much more detailed evaluation of the functional status of the inner ear. Further, the summating potential of the spiral ganglion (CAP) can be recorded with a much better signal-to-noise ratio. Thus, a number of diagnostic and therapeutic applications are available utilizing the apparatus and methods of the presently disclosed subject matter.

The presently disclosed subject matter provides for the direct recording of acoustically or mechanically evoked auditory potentials with a measuring device, such as for example one or more electrodes, placed within the cochlea. With regard to placement of the measuring device "within the cochlea", "inside the cochlea" or "intracochlear", the terms are meant to include not only placement of the device within the interior of the cochlea, but also within close proximity to the cochlea (e.g., in contact with the exterior of the cochlea), so long as the device is positioned sufficiently proximate the cochlea to detect an acoustically or mechanically evoked electrophysiologic response, as opposed to a far-field recording site distant from the cochlea. Although cochlear implants introduce an electrode into the cochlea, they are designed to directly stimulate auditory neural pathways and are not configured to record acoustically or mechanically evoked auditory potentials. In order to configure one of these devices to record acoustically or mechanically evoked auditory potentials, the electrical stimulation function can be disabled, and measurement electrodes can be triggered to measure auditory potentials in response to mechanical or acoustic stimulation.

Certain cochlear implants can include a feature for recording neural elements in the distal auditory nerve excited by electrical stimulation through the cochlear implant to verify correct device placement, but not to measure hair cell potentials. Thus, cochlear implants are used to stimulate auditory nerves electrically and, and in some instances record resulting electrical auditory potentials. Depending on the device manufacturer, recording systems are termed: NRT (neural response telemetry), NRI (neural response imaging), or ART (auditory nerve response telemetry) (Mason, 2004; Battmer et al., 2004; Shallop et al., 1999). However, none of these recording systems are designed to record acoustically or mechanically evoked auditory potentials. Instead, presently-available devices usually measure compound nerve action potentials from the spiral ganglion of the cochlear nerve, and therefore cannot provide data related to hair cell function. Also, currently available systems are only able to record electrically evoked potentials.

Thus, the presently disclosed subject matter differs significantly from present cochlear implant recording systems in that with the present subject matter, an acoustical or mechanical (rather than an electrical) stimulus is applied and an electrophysiologic response resulting from acoustically or mechanically evoked hair cell or neural activation is directly measured. An acoustic or mechanical stimulus will primarily activate (residual) intracochlear hair cells, rather than nerves proximal in the auditory system, as occurs with electrical stimulation by present cochlear implants. As such, if neural activation is measured as an electrophysiologic response to an acoustic or mechanical stimulus, it can be a surrogate marker of functionally linked hair cell activation. This provides direct information as to the functionality of hair cells and the geographic abundance of functioning hair cells.

Figure 2:
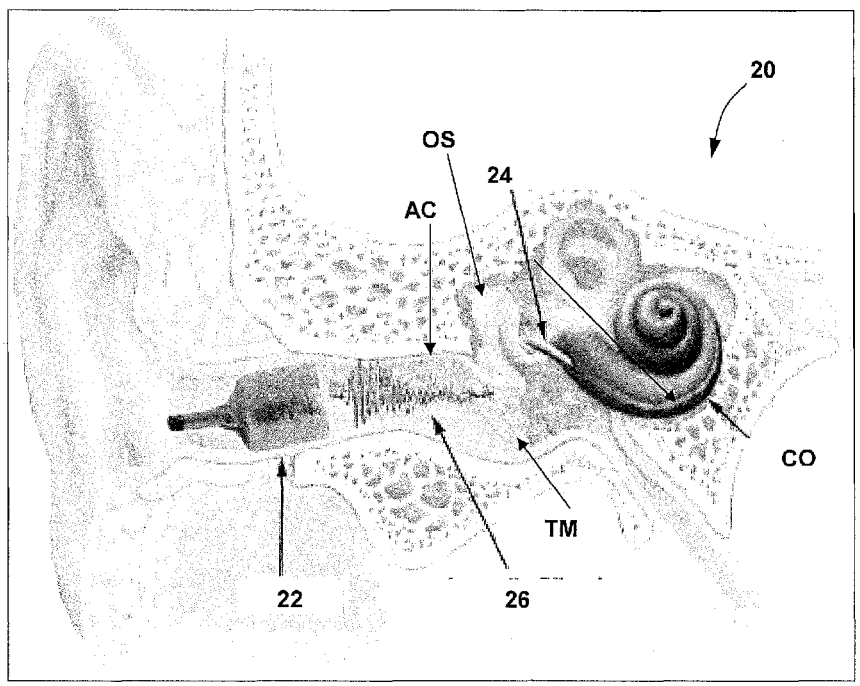
FIG. 2 is a schematic drawing showing an embodiment of the device of the presently disclosed subject matter for acoustic cochlear stimulation and intracochlear recording of acoustically or mechanically evoked potentials. In this embodiment of the presently disclosed subject matter, a speaker is placed within the external auditory canal to deliver an acoustic stimulus and a triggering mechanism synchronizes the auditory output with the electrophysiologic response measuring device, shown as a recording electrode array in this embodiment.

A device of the presently disclosed subject matter for recording acoustically or mechanically evoked potentials can include in some embodiments an intracochlear electrophysiologic response measuring device, such as for example a recording electrode or electrode array, that is coupled to and triggered with (or vice versa) an acoustic stimulator for generating an acoustic signal in the external auditory canal (FIG. 2). In some embodiments, the acoustic stimulator can comprise an electroacoustic device, which can include for example a generator for generating the acoustic signal and a speaker that transmits the acoustic signal. As used herein, however, "speaker" can refer to both a generator and speaker as a single device. The speaker can be positioned within the external auditory canal, or can be outside the auditory canal, such as for example a headphone or free-field speaker. The acoustic stimulator can generate as an acoustic signal, a sound wave, for example. In some embodiments, the acoustic signal may have a predetermined frequency or frequency range that changes to facilitate measurement of cochlear electrophysiologic responses at different frequencies (FIG. 1). For example, the acoustic stimulator can generate over a time period a range of different frequencies to provide a spectrum of cochlear function. In some embodiments, the frequency range of the acoustic signal can be from about 20 Hz to about 20,000 Hz. Atraumatic insertion and positioning of such a recording system into the cochlea can be accomplished utilizing hearing preservation surgical techniques, as would be understood by one of skill in the art. The same frequencies or frequency ranges may be generated by a mechanical stimulator to evaluate cochlear function at different frequencies.

With reference to FIG. 2, in one embodiment of an apparatus 20 for acoustic stimulation and electrophysiologic response measurement, as disclosed herein, apparatus 20 includes a speaker 22 as part of an acoustic stimulator and a recording electrode array 24 as an electrophysiologic response measuring device. In the illustrated example, electrode array 24 comprises an elongate and flexible structure that curls to match the contours of the region of the cochlea in which it is inserted. In FIG. 2, the outer wall of cochlea CO is shown in a semi-transparent manner so that electrode 24 is visible. Speaker 22 can (but not necessarily) be positioned in the external auditory canal AC and generates an acoustic signal 26 directed toward the cochlea CO. Acoustic signal 26 is transmitted from external auditory canal AC by way of the tympanic membrane TM and ossicles OS to cochlea CO. Upon transmission into cochlea CO, acoustic signal 26 is transformed into mechanical energy that can activate hair cells to generate an electrical potential, which is transmitted to the brain via nerve fibers. More specifically, hair cell activation results in cellular depolarization. Such activation secondarily results in cochlear nerve depolarization that is transmitted to the brain. Such depolarizing responses in both the cochlear hair cells and nerves can be generated by acoustic stimulation and can be measured. As such, electrode array 24 records the generation of an electrical potential by the hair cells or nerves. The recorded signal can be transmitted, for example wirelessly using radio waves, to a user for analysis.

An example of a device suitable for use as speaker 22 is the model number 019-746802, available from Viasys, Conshohocken, Pa., USA. Speaker 22 may be driven by an ABR device to generate acoustic stimuli. Examples of devices suitable for use as electrode 24 are Pulsar Ci100, (MED-EL, Innsbruck, Austria), Nucleus Freedom (Cochlear Corporation, Lane Cove, NSW, Australia), or 90K Hi Resolution cochlear implant system (Advanced Bionics Corp, Sylmar, Calif., USA).

As described above, in an alternate implementation, a mechanical stimulus may be utilized to evoke an auditory potential. In one example, a system to apply mechanical energy could be a direct drive system of the ossicular chain or the round window. Likewise, the oval window could be directly stimulated. An existing system suitable for applying mechanical energy could be the floating mass transducer (FMT) of the Vibrant Soundbridge (MED-EL, Innsbruck, Austria) or similar fully or semi-implantable devices applying mechanical energy to the acoustic system.

Figure 3:
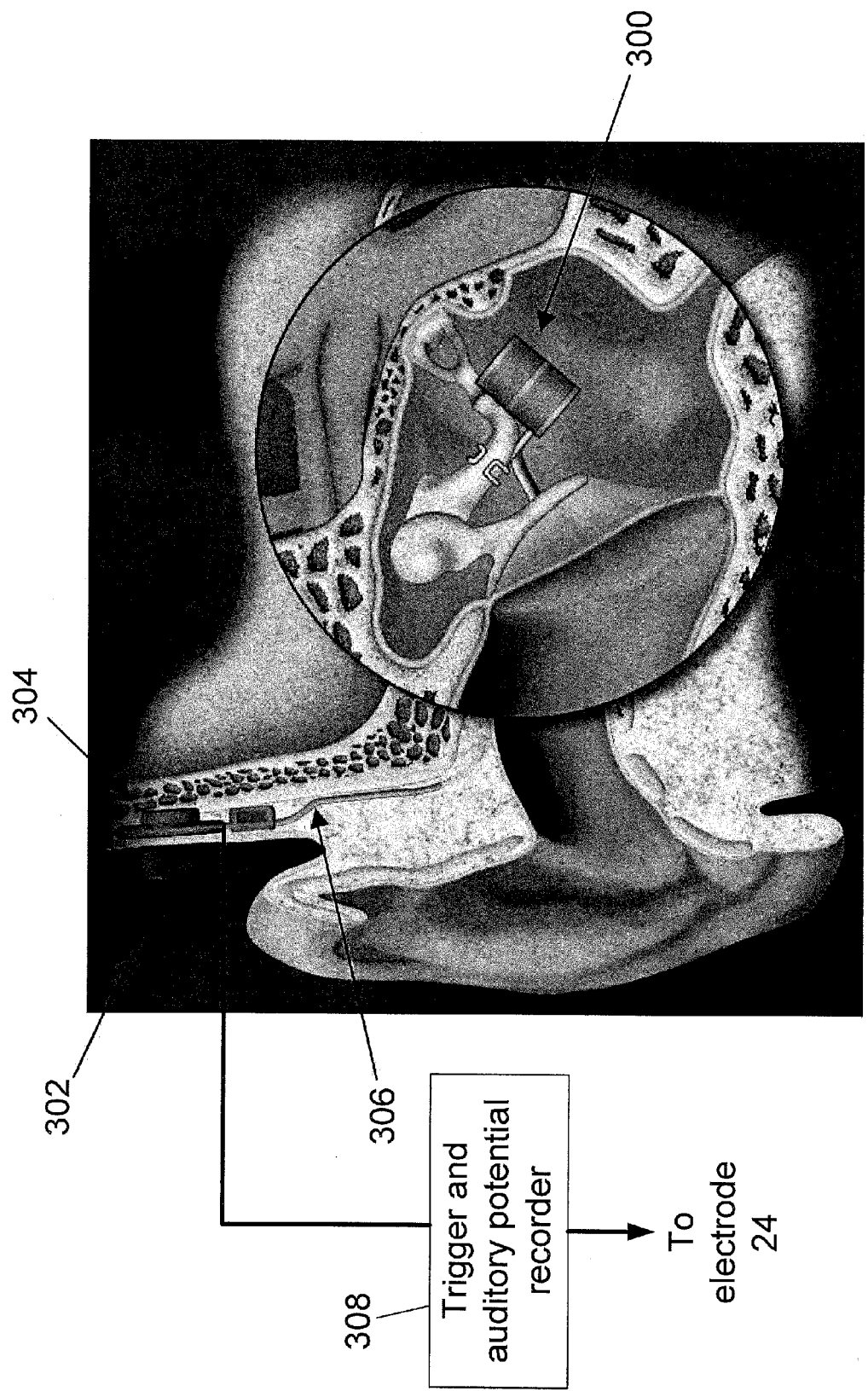
FIG. 3 is a schematic diagram illustrating a mechanical stimulator suitable for mechanically evoking auditory potentials according to an embodiment of the subject matter described herein.

FIG. 3 is a block diagram illustrating the FMT device and a trigger and audio potential recorder to record mechanically stimulated auditory potentials according to an embodiment of the subject matter described herein. Referring to FIG. 3, FMT device 300 is attached to one of the bones in the ossicular chain. An audio processor 302 encodes externally generated sound and communicates that sound to a subcutaneous receiver 304. Receiver 304 encodes the sound communicates the encoded sound to FMT device 300 via a conductor 306. FMT device 300 vibrates in response to external stimuli and thus transfers mechanical energy to the bone to which it is attached. Thus, in its normal mode of operation, the device illustrated in FIG. 3 functions as a hearing aid.

According to an embodiment of the subject matter described herein, the system illustrated in FIG. 3 can be used in combination with electrode 24 illustrated in FIG. 2 to mechanically evoke auditory potentials and to record those potentials. For example, audio processor 302 and/or receiver 304 may be configured to generate encoded audio signals such that FMT device 300 vibrates at predetermined frequencies.

One of audio processor 302, receiver 304, or conductor 306 may be coupled to trigger and auditory potential recorder 308 to trigger the recording of auditory potentials generated by electrode 24. Trigger and auditory potential recorder 308 may be coupled to electrode 24 to record auditory potentials generated in response to mechanical or auditory stimulation. Trigger and auditory potential recorder 308 may be implemented in hardware, software, firmware, or any combination thereof. In one embodiment, trigger and auditory potential recorder 308 may be implemented using a general purpose computing platform, such as a personal computer, with interfaces to the stimulus generation mechanism and to the recording electrode.

The subject matter described herein is not limited to using a floating mass transducer to mechanically stimulate an auditory potential. In an alternate implementation, another suitable device for use as a mechanical energy applicator could be a bone anchored hearing aid such as the BAHA hearing system (Cochlear Corporation, Lane Cove, NSW, Australia). Also, a conventional bone conduction hearing aid could be used to apply mechanical energy to the cochlea.

The electrophysiologic response-measuring device may be positioned within the cochlea so as to allow for measurement of acoustically or mechanically evoked electrophysiologic responses resulting from hair cell stimulation and/or nerve responses. In some embodiments, the electrophysiologic response-measuring device may be positioned in an intracochlear location or external the cochlea, but in close proximity to the cochlea (e.g., contacting the cochlea). Localized in an intracochlear position, the physiologic response measuring device can be located proximal to hair cells of the cochlea to better directly receive electrophysiologic responses. For example, in one embodiment an electrophysiologic response measuring device, shown in FIG. 4 as a cross-section of electrode array 24, can be positioned within the scala tympan±32 of the cochlea CO, which is adjacent the scala media SM (below scala vestibule SV) where hair cells HC reside. Positioning within the scala tympani ST allows for direct measurement of electrical potentials arising from either hair cell HC or neural activation and transmitted initially through hair cells to nerves HCN.

Figure 5:
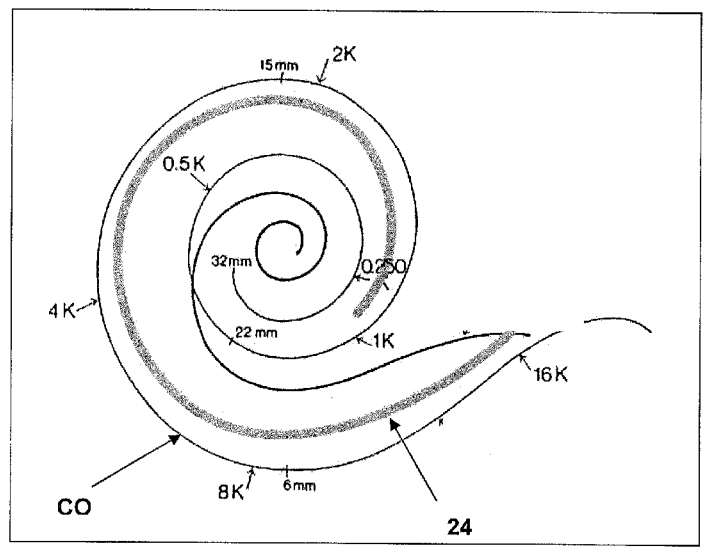
FIG. 5 is a schematic drawing showing an embodiment of electric acoustic stimulation (EAS) of the auditory system. The basal section of the cochlea (high frequencies) can be stimulated via a cochlear implant and if needed the apical section of the cochlea (low frequencies) can be stimulated via a conventional hearing aid (or without hearing aid if residual low frequency hearing is satisfactory).

In some embodiments, the electrophysiologic response measuring device can include at least one electrode contact for measuring an acoustically or mechanically evoked electrophysiologic response resulting from hair cell stimulation. In some embodiments, the electrophysiologic response measuring device can include a plurality of electrodes arranged in an array. This arrangement allows for measurement of hair cells across a portion or even the entire cochlea. Further, data from the individual electrodes in the array can be tracked, which provides information as to tonotopic functionality of the hair cells within the cochlea. Thus, in some embodiments, the electrode array can extend the entire length of the cochlea and in other embodiments, the electrode array extends along a portion of the cochlea, such as for example only along the basal portion of the cochlea to measure high-frequency hair cell stimulation (e.g., about 1,500-20,000 Hz) or only along the apical portion of the cochlea to measure low-frequency hair cell stimulation (e.g., about 200-600 Hz) (FIG. 1). FIG. 5 shows an intracochlear electrode array 24 implanted within the cochlea CO and extending partially, but not completely, within the cochlea CO for measurement of electrophysiologic responses resulting from hair cell stimulation.

In some embodiments, an electrode array adapted from a cochlear implant (with or without the other components of the cochlear implant) for stimulation of cochlear nerves can be utilized. Exemplary cochlear implants are described in detail in U.S. Pat. Nos. 4,400,590; 4,532,930; 4,592,359; 4,947,844; 5,776,172; 6,067,474; and 6,980,864, the disclosure of each of which is incorporated by reference herein in its entirety. In general, cochlear implant systems include an implanted receiver/stimulator connected to an implanted electrode array. The receiver/stimulator can deliver current to particular electrodes in the array that stimulate determined frequencies of the cochlear nerves in response to signals from an external acoustic receiver. In some cochlear implant systems, the implanted receiver/stimulator can further include a transmitter for telemetering electrode voltage, measured during stimulation, to an external receiver for monitoring and analysis as an indicator of proper operation of the implanted stimulator. Cochlear implant electrode arrays having capacity to also transmit measured voltages can be adapted for use with the presently disclosed subject matter. Rather than measure voltage applied by the stimulator, the electrode array can be utilized to measure and transmit acoustically or mechanically evoked electrophysiologic responses originating from activation of hair cells or neural elements, as disclosed herein. Thus, in some embodiments of the presently disclosed subject matter, the electrophysiologic response measuring device can include an electrode array derived from a cochlear implant (with or without other components of the implant) to measure acoustically or mechanically evoked electrical potentials from activated hair cells. For example, an existing cochlear implant used for electrical stimulation and response measurement can be modified to disable or omit the electrical stimulation function, to trigger the generation of auditory potentials, and to record the acoustically or mechanically evoked auditory potentials within a time window or windows that have a predetermined temporal relationship with the acoustic or mechanical stimulation.

In one implementation, a cochlear implant used for electrical stimulation and response measurement was modified to generate a trigger signal. The trigger signal was coupled to an external acoustic stimulator to trigger generation of an acoustic stimulus. The cochlear implant was then used to record auditory potentials generated within the cochlea in response to the acoustic stimulus. Exemplary data recorded in response to the stimulus will be described in detail below.

Figure 6:
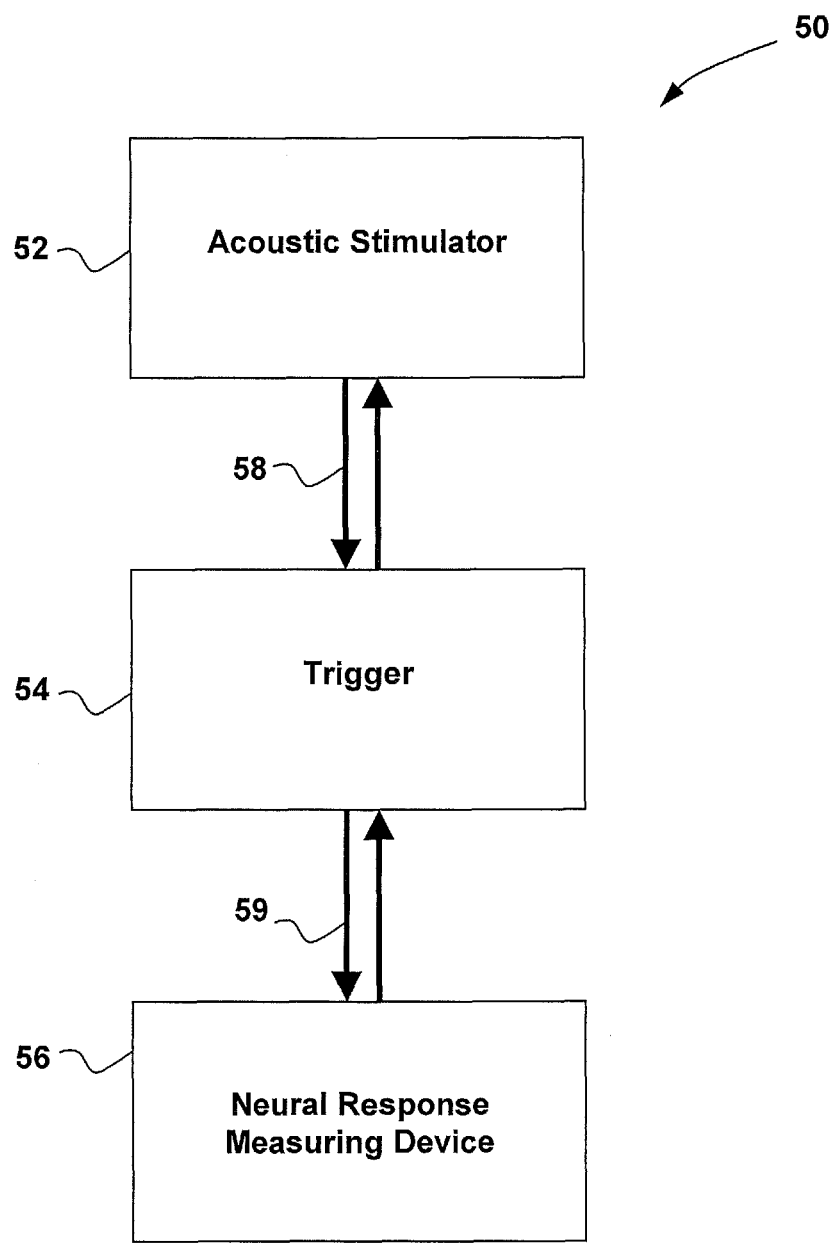
FIG. 6 is a flow chart illustrating interactions between a trigger, an acoustic or mechanical stimulator, and an electrophysiologic response-measuring device in one embodiment of the subject matter disclosed herein.

In some embodiments of the presently disclosed subject matter, the apparatus for acoustic or mechanical stimulation and electrophysiologic response measurement further comprises a trigger for facilitating communication between the acoustic or mechanical stimulator and the electrophysiologic response measuring device. For example, in the embodiment shown in FIG. 6, an apparatus 50 for acoustic stimulation and electrophysiologic response measurement includes an acoustic stimulator 52, such as for example a stimulator comprising speaker 22, in communication with an electrophysiologic response measuring device 56, such as for example a measuring device comprising electrode array 24, through a trigger 54. In one implementation, trigger 54 may be a signal generated by acoustic or mechanical stimulator 52 such that activation of acoustic stimulator 52 to generate an acoustic signal for stimulation of a cochlea activates measuring device 56. Measuring device 56 and/or an associated computer that stores responses to mechanical or acoustic stimuli may be timed to record evoked auditory potentials for a desired time period after acoustic or mechanical stimulator 52 generates the acoustic or mechanical signal. In an alternate implementation, electrophysiologic response measuring device 56 and acoustic or mechanical stimulator 52 may be controlled by a computer (not shown), and trigger 54 may be a software algorithm that activates electrophysiologic response measuring device 54 after activating acoustic stimulator 52. In yet another alternate implementation, trigger 54, may be a signal generated by neural response measuring device 56 that instructs acoustic or mechanical stimulator 52 to generate an acoustic or mechanical signal. After activating the trigger signal, neural response measuring device 56 and/or a computer associated with neural response measuring device 56 may record evoked auditory potentials for a predetermined time window related to the length of acoustic or mechanical stimulation Thus, trigger 54 facilitates a recording by measuring device 56 following each acoustic signal at a certain time interval (e.g., a sampling window). Single recordings or continuous recordings after repetitive acoustic stimuli can be performed, if desired. As shown by arrows 58 and 59 in FIG. 5, trigger 54 can be activated in response to either activation of acoustic or mechanical stimulator 52 to generate an acoustic or mechanical signal, or in response to activation of measuring device 56 to begin measuring a sampling window of electrophysiologic responses. In the latter case, trigger 54, after detecting activation of measuring device 56, activates acoustic or mechanical stimulator 52 to generate an acoustic or mechanical signal. In this manner, the sampling window begins recording a set time period prior to activation of acoustic or mechanical stimulator 52.

Software for management of trigger 54 can, in some embodiments, be modified from existing cochlear implant software. Additional modifications of the software, if desired, can include an acoustic or mechanical stimulus generator (e.g., pure-tones, clicks, as well as other forms of acoustic waveforms or corresponding mechanical waveforms) and a module that can move the recording window (usually a relatively time-constrained interval of from about 0.2 to about 100 milliseconds (ms)) in relation to the acoustic signal, which can in some embodiments facilitate activation of the trigger. Another embodiment for software instructions for recording intracochlear potentials includes instructions for increasing the duration of the recording time period, such as for example to provide a sampling window of less than about 100 ms, such as from about 0.2 ms to about 100 ms, from about 2 ms to about 10 ms, or from about 4 ms to about 5 ms. Depending on memory storage, however, constraints may exist as to how much data can be stored in the internal memory and to the sampling rate of measuring device 56 (temporal resolution), for which one of skill in the art would be familiar and take into consideration when balancing sampling window size, timing and resolution needs.

The presently disclosed subject matter further provides methods of utilizing an apparatus as disclosed herein for generating an acoustic or mechanical signal as an acoustic or mechanical stimulus for a cochlea of a subject and measuring an electrophysiologic response by the cochlea to the acoustic or mechanical stimulus. As disclosed in detail herein, the apparatus can include an acoustic or mechanical stimulator for generating the acoustic signal and an electrophysiologic response measuring device for measuring the acoustically or mechanically evoked electrophysiologic response to the acoustic stimulus. In some embodiments, the stimulator is an acoustic stimulator comprising a sound applicator including at least one speaker for generating sound waves. Further, the acoustic stimulator can be positioned within the external auditory canal, as shown in FIG. 2, to direct the acoustic stimulus toward the cochlea to be measured. Additionally, the acoustic stimulator can in some embodiments be located outside the external auditory ear canal, to generate an acoustic stimulus externally, such as by way of free-field acoustics or headphones, for example. The acoustic stimulus can stimulate functioning hair cells in the cochlea to generate an electrical potential transmitted through auditory nerves (e.g., nerves of the spiral ganglion). In other embodiments, the cochlea can be stimulated by application of mechanical energy to the acoustic system. Specifically, mechanical energy can be applied to the ossicular chain or any other parts of the auditory system. Mechanical energy can be applied via a bone conductor or other suitable mechanical device such as an active middle ear implant or a bone anchored hearing aid.

The electrophysiologic response-measuring device can be positioned within the cochlea (see FIG. 4) to facilitate direct measure of the acoustically or mechanically evoked electrophysiologic response (e.g., hair cell or neural potentials) and provide an assessment of hair cell function and viable hair cell distribution, which are indicative of hearing function. Determination of the type and degree of hearing impairment using an apparatus as disclosed herein can further facilitate selection of a hearing impairment treatment therapy. In some embodiments, a hearing impairment is determined by measuring an electrophysiologic response by the cochlea to an acoustic or mechanical signal. Determination of the hearing impairment then facilitates selection of an appropriate and tailored treatment for the hearing impairment, which can provide the benefits of a more effective treatment and one that preserves residual hearing while treating the hearing impairment, as described in further detail below.

Applications for an intracochlear recording system as disclosed herein that can measure acoustically or mechanically evoked electrophysiologic responses include, for example, real-time monitoring for hearing preservation attempts during cochlear implant surgery. Additional applications include, for example, diagnostic assessments during other surgeries of the inner ear (skull base surgery (McElveen et al., 1991), etc.) or even tailoring the approach to a variety of cochlear-specific therapies. Directing therapies to specific anatomic regions and assessing the ongoing results of therapies (Light & Silverstein, 2004; Schwaber, 2002) can also be achieved utilizing the presently disclosed apparatus and methods. Further, from a research perspective, the presently disclosed subject matter provides multiple opportunities for better understanding the validity of a variety of commonly held assumptions in the hearing sciences.

One embodiment for utilizing an intracochlear recording system as disclosed herein for measuring acoustically or mechanically evoked electrophysiologic responses is now described as a non-limiting illustrative example of how the apparatus disclosed herein can be implemented in a subject. The presently disclosed apparatus allows for direct assessment of functionality of hair cell populations and neural elements from within the cochlea, which can facilitate mapping of tonotopic functionality in a subject. The apparatus can include an electrophysiologic response measuring device with an intracochlear electrode array or a single electrode. The array or the single electrode can be inserted into the cochlea through the external auditory canal and then through the round window under either general or local anesthesia. To advance and withdraw the electrode within the cochlea, manual or servo assisted techniques can be used. Anatomically, the posterior external auditory canal wall and the basal cochlear turn (basal scala tympani) encompass almost a 90° angle. Since the basal cochlear turn does not follow the direction of the bony posterior canal wall, a tungsten-rod for stabilizing and deflecting the extracochlear part of the insertion electrode can be used. The insertion tool can thus act like a deflection instrument to guide the electrode atraumatically into the scala tympani of the cochlea. After replacing the tympanic membrane (or the tympanomeatal flap), an acoustic stimulator including a small speaker system can be placed in the auditory canal to provide acoustic stimulation. Likewise, any method for the application of mechanical energy as outlined above can be used. Recordings of electrophysiologic responses can be made from a variety of locations within the cochlea either using multiple electrodes on a single array or a single electrode that is advanced to a variety of different anatomical locations. Waveforms can if desired be extracted through averaging, although very beneficial signal-to-noise ratios already result from the intracochlear placement of the recording electrode(s) (i.e. the recording electrode is very close to the origin of the biological signal).

Such precise measurements can then be used to anatomically target therapies within the cochlea. Currently, approaches to cochlear hearing loss rely upon global or systemic treatments to the entire cochlea. As many subjects have hearing impairments that only affect specific intracochlear regions, this approach can be utilized for directed intracochlear therapy. For example, intracochlear devices (e.g., cochlear implants), drugs (e.g., small molecule pharmaceuticals), gene therapies, or stem cells (see e.g., Tang et al., 2006) can be delivered to specific locations within the cochlea based on the precise functional parameters obtained using the apparatus and methods disclosed herein.

As described above, methods of selecting a hearing impairment treatment therapy based on measurement of an acoustically or mechanically evoked electrophysiologic response and determination of a hearing impairment are provided. For example, currently, cochlear implants stimulate the cochlear (e.g., auditory, acoustic) nerve in regions of the cochlea where hair cell populations have been lost. Since many cases of SNHL involve high frequency losses, partial implantation of an intracochlear electrode in the basal (i.e., first or lower) portion of the cochlea can electrically stimulate high frequency nerve fibers. If hair cell function in the low frequency regions is preserved in a subject treated for high frequency hearing impairment, conventional amplification (e.g., hearing aids) can be used in these regions. By treating only the impaired hair cell regions of the cochlea, residual hearing is preserved. This principle of bi-modal acoustic stimulation using both a cochlear implant and a hearing aid has been termed electric-acoustic stimulation (EAS) (von Ilberg et al., 1999; U.S. Pat. No. 6,231,604) or hybrid cochlear implantation (Gantz & Turner, 2003) (FIG. 3). Experimental clinical studies have demonstrated that EAS can provide better speech perception results than with the cochlear implant alone, especially in a noisy environment. Thus, EAS can improve speech understanding in common listening situations with background noise where cochlear implants alone may not provide acceptable results.

Recent studies have suggested that the effectiveness of EAS depends on the amount of residual hearing that exists following surgery (Gantz & Turner, 2003; Gantz & Turner, 2004; Gstoettner et al., 2004; Kiefer et al., 2005). This depends, in large part, on the ability of the cochlear implant surgeon to accomplish atraumatic electrode insertion using currently available arrays. Limited clinical studies of EAS have been able to document that complete hearing preservation is possible in about 50% of subjects (Gstoettner et al., 2004; Kiefer et al 2004; Gantz et al., 2005; James et al., 2005). Another large fraction of study subjects lose significant amounts of residual hearing but retained some residual function. Unfortunately, the factors that determine hearing preservation during and following cochlea implantation are not known.

Based on the teachings of the presently disclosed subject matter that acoustically or mechanically evoked auditory potentials are related to residual cochlear function, the presently disclosed apparatus for measuring acoustically or mechanically evoked auditory potentials can be used as a tool to measure residual cochlear function during cochlear implantation. The information generated by apparatus disclosed herein can be used to provide a real-time direct measure of the feasibility of bi-modal stimulation during surgery and determine the precise depth of electrode implantation needed for subjects with residual functioning hair cell populations.

As previously described, EAS relies on the ability of the implanting surgeon to preserve residual cochlear function. Unfortunately, prior to the presently disclosed subject matter, there were no real-time or intraoperative measures available to assess whether and how much cochlear function had been preserved. Thus, the surgeon was left to undertake the surgery and assume the hearing had been preserved. Following recovery, hearing would be assessed weeks later. If hearing is preserved, bi-modal stimulation is undertaken. When hearing has been lost, auditory stimulation can only be provided by the implant. Since the electrodes used for bi-modal stimulation are significantly shorter than those used for conventional full cochlear implantation, revision implantation with a longer electrode array must be considered (Battmer et al., 2004).

Currently available technologies are not able to measure cochlear function accurately because current techniques use relatively "far-field recording" methods. Since the signal to noise ratio of the far-field set up is relatively poor, numerous cycles and signal averaging are required. This also creates a sum potential of most parts of the cochlea instead of a certain area inside the cochlea, which precludes mapping of tonotopic functionality.

Thus, measuring cochlear function during cochlear implantation can assist the surgeon in determining whether EAS is feasible while still in the operating room. For example, if complete loss or significant attenuation of acoustically or mechanically evoked auditory potentials is observed during surgery, hearing preservation would be considered unlikely and full electrode insertions with a standard, cochlear implant electrode would be prescribed. Alternatively, if tonotopic mapping using the present apparatus and methods indicates residual hearing, then an appropriately-sized and positioned cochlear stimulating electrode can be implanted and an EAS plan implemented for the subject.

As noted above, EAS relies on the preservation of hearing during surgery (Gstoettner et al., 2004; Kiefer et al., 2005). Again, the basic concept of EAS is that those areas of the cochlea with residual hair cell populations can be used for acoustic hearing (with or without amplification), whereas electrical stimulation can cover areas without functioning hair cells. Thus, the ideal EAS electrode array insertion would be that situation where the distal (i.e. deepest, apical cochlear sections) electrode would be advanced just up to the point where hair cell populations are present. This would thereby avoid either a gap or an overlap between the two stimulation paradigms (i.e. acoustic and electric). Unfortunately, such precision may not be possible with current technology since hair cell populations and locations cannot be directly assessed. Rather, a one size fits all approach is currently being used. This approach relies on the assumption that all hearing losses (and thus hair cell populations) are similar among subjects (EAS candidates). This of course is not the case. Currently, there are two different electrode array lengths being used in research studies (a 10 mm or a 20 mm array (von Ilberg et al., 1999; Gstoettner et al., 2004; Kiefer et al., 2005; Fraysse B et al., 2006; Adunka et al., 2004; Adunka et al., 2004)). Standard cochlear implant electrode arrays also vary in length but may be as long as 31.5 mm. However, for EAS, these proposed insertion depths represent relatively arbitrary numbers with little basis for choice, except for the notion that deeper implantations cause an increase in intracochlear trauma and thus increase the likelihood of further hearing loss due to damage to existing residual hair cell populations.

Thus, the presently disclosed subject matter provides for real-time, intraoperative monitoring of cochlear function during electrode insertion. When the distal most electrode contact is advanced up to the residual hair cell populations, insertion ceases, and residual hair cell populations are preserved. For example, if functioning hair cell populations are identified using the apparatus and methods disclosed herein after 7 mm of insertion, then the subject would have a 7 mm electrode array (or slightly shorter) implanted. By contrast, if functioning hair cell populations are identified at 24 mm, then a longer array (e.g., up to 24 mm in length) can be used. Thus, utilizing the presently disclosed apparatus and methods for determining residual hearing with specificity, a customized electrode array designed to the particular needs of the individual subject can be used, rather than an electrode of arbitrary standard length, which can provide optimal hearing assistance needed while avoiding damage to residual hearing still available to the subject.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

The presently disclosed subject matter provides apparatus and methods for acoustic or mechanical stimulation of a cochlea and for recording acoustically or mechanically evoked auditory activity from hair cells and auditory neural structures using one or more electrodes positioned within the cochlea. Some cochlear implants provide an intracochlear recording device, however, these are not designed to measure acoustically evoked electrophysiologic responses. Development of such a recording device, either by modifying currently available cochlear implants, or by providing a diagnostic intracochlear device can provide a broad functional assessment of the peripheral (cochlear and spiral ganglion) auditory system. The following experiments set forth in the Examples can be carried out to establish the presently disclosed stimulation/recording paradigm in a diagnostic intracochlear recording device, which can include as one component all or portions of a modified cochlear implant.

Example 1

Establish Engineering Parameters of a Stimulation/Recording Set-Up Using Currently Available Cochlear Implants Since certain cochlear implants can include intracochlear recording systems, modifications to establish recording of acoustically evoked auditory potentials can be achieved. The modifications can provide inclusion of a triggering mechanism between the acoustic or mechanical stimulation and the intracochlear electrophysiologic measurements. The modification can further include a function to turn-off the electrical stimulation usually present in cochlear implants used to measure electrically evoked auditory potentials. Thus, the acoustic stimulus can be positioned in temporal relationship to the intracochlear recording procedure without recording electrically evoked potentials, such that only acoustically or mechanically evoked potential is measured.

Initial experiments can be performed to establish the trigger for the acoustic or mechanical output and the recording signals. An aim of these experiments is to determine the correct timing for the recording after the acoustic stimulus has been triggered.

Furthermore, normative data can be established in subjects who have received a cochlear implant and show some residual hearing on the implanted ear. Some hearing remnants can be recorded in about 50% of subjects who have been implanted with electrode arrays. Since cochlear microphonics can sometimes be recorded in profoundly deaf individuals, potentials can be recordable even in subjects who have lost residual hearing due to cochlear implantation (or who did not show residual hearing prior to implantation).

Subjects with auditory neuropathy can be measured to determine acoustically or mechanically evoked potentials from hair cells in isolation, thus providing a clean signal. These subjects have no synchronized neural response that may artifactually obscure the early hair cell and neural responses. Subjects with increasing residual hearing can then be tested, after a baseline waveform of hair cell neural responses is determined in the neuropathy subjects. Inverting click or mechanical stimulus polarity in both groups can be useful for determining hair cell response versus early neural responses.

Example 2

Establish Normative Data on the Functional-Anatomical Correlations of the Intracochlear-Recorded Acoustically or Mechanically Evoked Potentials with Conventional Behavioral Audiometry For this Example, each cochlear implant recipient can undergo testing both during and after cochlear implantation at different intervals. For subjects with residual hearing, correlations between conventional behavioral audiometry and acoustically or mechanically evoked intracochlear recordings can be sought. This way, information about the range of acoustically or mechanically evoked auditory potentials in ears with various degrees of residual hearing can be sought. For instance, if hearing is present after implantation at a given frequency, measurements can be made with the device described herein to identify those intracochlear regions that have electrophysiologic responses present in response to the same acoustic signal. Correlating these behavioral responses with the acoustically generated electrophysiologic measures generated with the device described herein allows validation or even rediscription of the tonotopical arrangement of the cochlea.

Example 3

Development of an Intracochlear Diagnostic Recording System for Sensorineural Hearing Loss The present Example relates to the development of an intracochlear recording device for diagnostic purposes alone or coupled with a therapeutic treatment, such as a drug-delivery system, as disclosed herein. The basis for such a system is to measure electrical activity of hair cells and auditory neural structures in particular segments of the cochlea and specifically treat intracochlear locations pharmacologically (e.g., with neural growth factors, apoptotic inhibitors, corticosteroids).

Animal experiments can demonstrate the feasibility and safety of short-term placements of intracochlear recording electrodes without causing hearing loss. Drug-delivery mechanisms can undergo feasibility and safety testing using animal experiments as well. The effects of intracochlear drug delivery on cochlear function and intracochlear morphological integrity have been studied previously (see e.g., Chen et al., 2006; Prieskorn & Miller, 2000).

Figure 4:
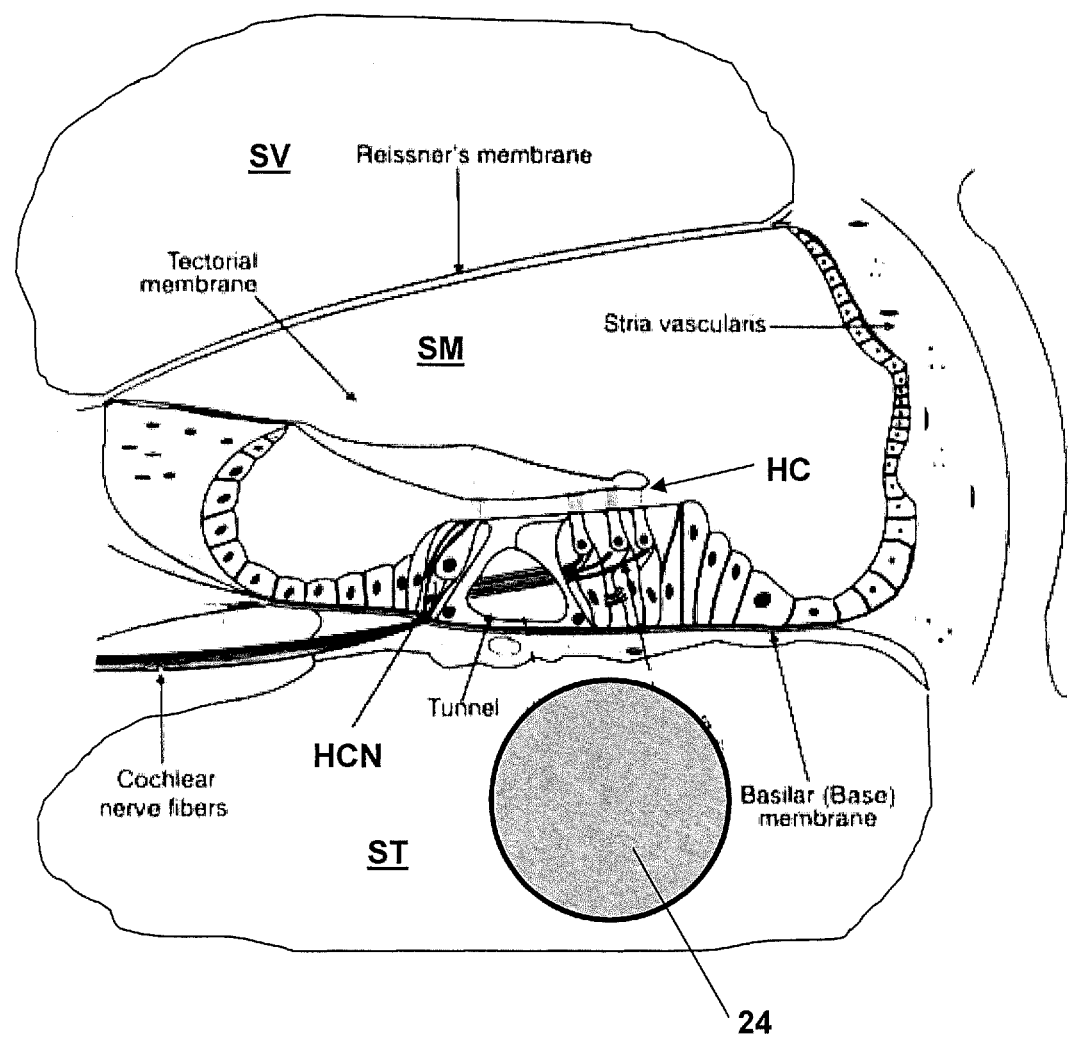
FIG. 4 is a schematic cross-sectional drawing of a cochlea showing positioning of an electrophysiologic response measuring device for measuring acoustically or mechanically evoked cochlear potentials. In this embodiment, the measuring device comprises an electrode array positioned within the scala tympani of the cochlea for measuring acoustically or mechanically evoked potentials derived from activation of hair cells or neural elements, which are proximate to the electrode array.

Preliminary data indicate that small and flexible electrodes can be safely inserted into the scala tympani of the cochlea without causing acute hearing loss (see e.g., FIG. 4). It is further noted that if the electrode is immediately withdrawn, no permanent damage to intracochlear structures will likely result. Thus, the etiology of hearing loss in cochlear implantation is probably due to slow-acting mechanisms (e.g., apoptotic mechanisms) rather than a result of acute hair cell loss immediately after electrode insertion (Adunka et al., 2006).

Feasibility and safety studies on humans can include subjects with pronounced sudden sensorineural hearing loss lacking adequate benefit from steroids applied immediately after the onset of hearing loss. In such a clinical scenario, the subject can potentially benefit from intracochlear application of corticosteroids. As long as hearing function is considered "non-functional" on that ear, intracochlear insertion of a diagnostic/drug-delivery device would be considered safe.

Example 4

Intraoperative Measurements of Acoustically Evoked Electrical Potentials

The present Example discloses clinical data showing measurement of acoustically evoked potentials (EP) measured intracochlearly that follow an acoustic tonal stimulus.

Figure 7:
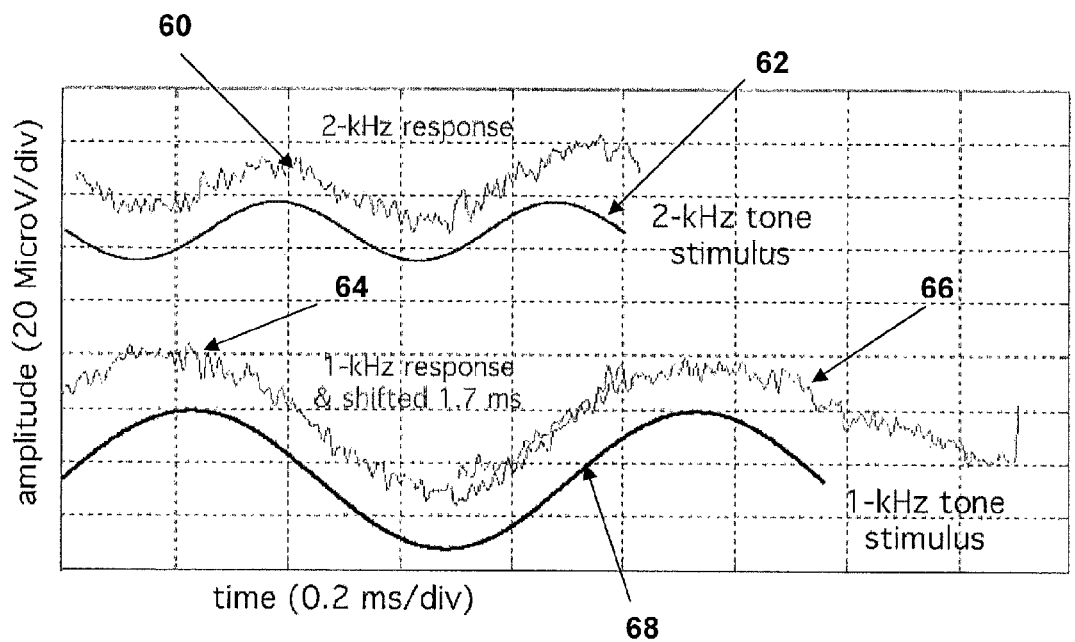
FIG. 7 is a graph showing measurements of responses achieved after acoustic stimulation of the cochlea at different frequencies (1 kHz and 2 kHz).

FIG. 7 shows results from one electrode obtained from acoustically-stimulating hair cells and measuring electrophysiologic response using an electrode array inserted in the cochlea of a human subject. The electrode utilized for deriving the data of FIG. 7 sits in the basal and middle cochlear turns; the corresponding frequency is assumed to be about 1000 Hz. Trace 60 is the measured electrical response to a 2-kHz tone acoustic stimulus used, which is plotted on the graph as waveform 62 for comparison. Traces 64 and 66 are measured electrical responses to a 1-kHz acoustic stimulus, which is plotted on the graph as waveform 68 for comparison. Trace 66 was taken 1.7 ms 'after' trace 64 (i.e., a delay was introduced before the measurement for those data), and the phase of the response shifted by 0.7 ms, as predicted. The data traces shown in FIG. 6 were processed for clarity of signal;

however, the unprocessed signals also showed a clear response to the acoustic signal.

As set forth above, an electrophysiologic response measurement device 56 can be a modified cochlear implant or a dedicated diagnostic device that is designed to be inserted in the cochlea for diagnostic purposes and then withdrawn. In either case, the electrophysiologic measurement device may be used to measure cochlear trauma cause by insertion of the device into the cochlea. For example, if the device is being inserted in the cochlea, acoustically evoked auditory potentials can be recorded at different times and levels of insertion. If the response measurement for the same cochlear region worsens from one time to another, the degradation in response may indicate cochlear trauma caused by impingement of the device on a cochlear structure. In response to detecting such a degradation, the implant or diagnostic device may be withdrawn to reduce the impingement on the cochlea or other factor that contributed to the response degradation. The procedure of measuring acoustically evoked auditory potentials during insertion can be used to distinguish between reversible and irreversible hearing loss. For example, a loss caused by impingement during insertion may be reversible by withdrawal of the diagnostic or implantation electrode. Similarly, an evoked auditory potential that is constant for different times during insertion may indicate an irreversible hearing loss.

In addition to being usable for measuring an acoustically evoked response and intracochlear drug delivery, an electrophysiologic response measurement device, including a dedicated diagnostic device or a modified cochlear implant, may further be used for delivering diagnostic electrical stimulation to the cochlea. For example, in regions of the cochlea where hair cell function is degraded or lost, but auditory nerve function is intact, the electrophysiologic response measurement device can be used to deliver a diagnostic electrical stimulation to such regions and record the resulting evoked auditory potential.

REFERENCES

The references listed below, as well as all references cited in the specification, are incorporated herein by reference to the extent that they supplement, explain, provide a background for, or teach methodology, techniques, and/or compositions employed herein.

Adunka O et al., *Acta Otolaryngol* 2004; 124:807-812.
Adunka O et al., *Laryngoscope* 2004; 114:1237-1241.
Adunka O et al., *Laryngoscope*. 2006; 116(6):1017-20.
Battmer R D et al., *Int J Audiol* 2004; 43 Suppl 1:S10-15.
Chen Z et al. *J Neurosci Methods* 2006; 150(1):67-73.
Fraysse B et al., *Otol Neurotol* 2006; 27:624-633.
Gantz B J & Turner C, *Laryngoscope* 2003; 113:1726-1730.
Gantz B J & Turner C. *Acta Otolaryngol* 2004; 124:344-347.
Gantz B J et al., *Laryngoscope* 2005; 115:796-802.
Gstoettner W et al., *Acta Otolaryngol* 2004; 124:348-352.
James C et al., *Acta Otolaryngol* 2005; 125:481-491.
Kemp D T, *Hear. Res.* 1986; 22:95-104.
Kiefer J et al., *Acta Otolaryngol* 2004; 124:272-280.
Kiefer J et al., *Audiol Neurootol* 2005; 10:134-144.
Light J P & Silverstein H., *Curr Opin Otolatyngol Head Neck Surg* 2004; 12:378-383.
Mason, *Int J Audiol* 2004; 43 Suppl 1:S33-38.
McElveen J T et al., *J Laryngol Otol* 1991; 105:34-37.
Prieskorn D M & Miller J M, *Hear. Res.* 2000; 140(1-2):212-5.
Schwaber M K, *Otolaryngol Clin North Am* 2002; 35:287-295, vi.
Shallop J K et al., *Laryngoscope* 1999; 109:1755-1759.
Tang L S et al. *IUBMB Life* 2006; 58(9):525-530.
U.S. Pat. No. 4,400,590.
U.S. Pat. No. 4,532,930.
U.S. Pat. No. 4,592,359.
U.S. Pat. No. 4,947,844.
U.S. Pat. No. 5,776,172.
U.S. Pat. No. 6,067,474.
U.S. Pat. No. 6,231,604.
U.S. Pat. No. 6,980,864.
Von Ilberg C et al., ORL J *Otorhinolaryngol Relat Spec* 1999; 61:334-340.

It will be understood that various details of the presently disclosed subject matter may be changed without departing from the scope of the present subject matter. Furthermore, the foregoing description is for the purpose of illustration only, and not for the purpose of limitation.

What is claimed is:

1. An apparatus for acoustic stimulation and electrophysiologic response measurement of a cochlea or auditory nerve, comprising:
   a stimulator, configured to generate one of an acoustic and a mechanical signal; and
   an electrode array positionable within a cochlea of a human subject directly adjacent to hair cells in the cochlea and configured to directly measure an electrophysiologic response of the hair cells directly adjacent to the electrode array to the stimulating signal, wherein the electrophysiologic response includes a cochlear microphonic potential; and
   a computer for recording an indication of a geographic abundance of functioning hair cells within the cochlea.

2. The apparatus of claim 1 wherein the stimulator comprises a speaker configured to generate the acoustic signal.

3. The apparatus of claim 1 wherein the stimulator comprises one of:
   a vibrotactile stimulator for generating a mechanical signal and for applying the signal to a portion of the patient's inner ear;
   a direct drive system for the ossicular chain;
   a bone anchored hearing aid; and
   a bone conduction hearing aid.

4. The apparatus of claim 1 wherein the electrode array comprises a modified cochlear implant.

5. The apparatus of claim 1 wherein the electrode array comprises a diagnostic electrode array that is not a cochlear implant and that is usable for diagnostic purposes alone or in combination with intracochlear drug delivery.

6. The apparatus of claim 1 wherein the electrode array is configured to be positioned within the cochlea for measurement of the electrophysiologic response and is thereafter configured to be withdrawn from the cochlea.

7. The apparatus of claim 1 wherein the electrode array is configured to measure a summating potential.

8. The apparatus of claim 1 wherein the electrode array is configured to measure a compound action potential (CAP).

9. The apparatus of claim 1 wherein the electrode array is configured to record the cochlear microphonic potential for a cochlear implant recipient who has lost residual hearing.

10. The apparatus of claim 1 wherein the electrode array is configured to measure at least one acoustically or mechanically evoked intracochlear recording for a cochlear implant recipient during implantation and at least one acoustically or mechanically evoked intracochlear recording for the cochlear implant recipient after implantation.

11. The apparatus of claim 1 wherein the electrode array is configured to measure cochlear trauma caused by insertion of the device into the cochlea.

12. The apparatus of claim 1 wherein the electrode array is configured to deliver diagnostic electrical stimulation to the cochlea.

13. An apparatus for acoustic stimulation and electrophysiologic response measurement of a cochlea or auditory nerve, comprising:
- a stimulator configured to generate one of an acoustic and a mechanical signal;
- an electrode array positionable within a cochlea of a human subject directly adjacent to hair cells within the cochlea and configured to measure an electrophysiologic response of the hair cells directly adjacent to the electrode array to the stimulating signal and wherein the electrode array comprises a diagnostic device; and
- a computer for recording an indication of a geographic abundance of functioning hair cells within the cochlea.

14. A method of measuring a cochlear electrophysiologic response to an acoustic signal, comprising:
- stimulating a cochlea of a human subject with one of an acoustic signal and a mechanical signal;
- positioning an electrode array within the cochlea directly adjacent to hair cells within the cochlea;
- measuring an electrophysiologic response of the hair cells directly adjacent to the electrode array to the acoustic signal using the electrode array, wherein the electrophysiologic response comprises a cochlear microphonic potential; and
- recording, using a computer, an indication of geographic abundance of functioning hair cells within the cochlea.

15. The method of claim 14 wherein stimulating the cochlea comprises acoustically stimulating the cochlea with an acoustic stimulator.

16. The method of claim 14 wherein stimulating the cochlea comprises using one of:
- a vibrotactile stimulator for generating a mechanical signal and for applying the signal to a portion of the patient's inner ear;
- a direct drive system for the ossicular chain;
- a bone anchored hearing aid; and
- a bone conduction hearing aid.

17. The method of claim 14 wherein the electrophysiologic response measuring device comprises a modified cochlear implant.

18. The method of claim 14 wherein the electrode array comprises a diagnostic intracochlear device that is not a cochlear implant and that is usable for diagnostic purposes alone or in combination with intracochlear drug delivery.

19. The method of claim 14 comprising measuring, using the electrode array, electrophysiologic responses of the cochlea during a residual hearing test and identifying intracochlear regions that have electrophysiologic responses to a same acoustic signal used in the residual hearing test.

20. The method of claim 14 wherein the electrode array is positioned within the cochlea and is thereafter withdrawn from the cochlea.

21. The method of claim 14 wherein the electrophysiologic response includes a summating potential.

22. The method of claim 14 wherein the electrophysiologic response includes a compound action potential (CAP).

23. The method of claim 14 wherein the cochlear microphonic potential is recorded for a cochlear implant recipient who has lost residual hearing.

24. The method of claim 14 comprising identifying, using the electrophysiologic response measured by the electrode array, a region of the cochlea where hair cell function is degraded or lost but where auditory nerve function is intact.

25. The method of claim 24 comprising, in response to identifying the region of the cochlea where hair cell function is degraded or lost, but auditory nerve function is intact, using the electrode array to deliver electrical stimulation to the region.

26. The method of claim 14 comprising measuring, using the electrophysiologic measurement device, cochlear trauma caused by insertion of the device into the cochlea.

27. The method of claim 14 comprising delivering, using the electrophysiologic response measurement device, electrical stimulation to the cochlea.

* * * * *